United States Patent
DeGonia et al.

(10) Patent No.: US 8,299,003 B2
(45) Date of Patent: *Oct. 30, 2012

(54) COMPOSITION COMPRISING A SULFUR-CONTAINING, PHOSPHORUS-CONTAINING COMPOUND, AND/OR ITS SALT, AND USES THEREOF

(75) Inventors: David J. DeGonia, Midlothian, VA (US); Chip Hewette, Richmond, VA (US); Roger M. Sheets, Glen Allen, VA (US); Ronald L. Phillips, Richmond, VA (US); John T. Loper, Richmond, VA (US)

(73) Assignee: Afton Chemical Corporation, Richmond, VA (US)

( * ) Notice: Subject to any disclaimer, the term of this patent is extended or adjusted under 35 U.S.C. 154(b) by 1143 days.

This patent is subject to a terminal disclaimer.

(21) Appl. No.: 11/372,183

(22) Filed: Mar. 9, 2006

(65) Prior Publication Data

US 2007/0142249 A1  Jun. 21, 2007

Related U.S. Application Data

(60) Provisional application No. 60/734,757, filed on Nov. 9, 2005.

(51) Int. Cl.
*C07F 9/6571* (2006.01)
*C07F 9/02* (2006.01)
*C10M 153/00* (2006.01)

(52) U.S. Cl. ......... 508/422; 508/187; 508/192; 558/164
(58) Field of Classification Search .................. 508/422, 508/192, 187; 558/164

See application file for complete search history.

(56) References Cited

U.S. PATENT DOCUMENTS 2,063,629 A   12/1936   Rosenmund
(Continued)

FOREIGN PATENT DOCUMENTS

EP   0459656   12/1991
(Continued)

OTHER PUBLICATIONS

Said, Musa A., et al., "Reactivity of cyclic arsenites and phosphites: X-ray structures of bis(5,5-diemthyl-1,3,2-dioxarsenan-2-yl)ether and bis(2,4,8,10-tetra-*tert*-butyl-12H-dibenzo[d,g]dioxarsenocin-6-yl)ether," *J. Chem. Soc. Perkin Trans* 1, 22: 2945-51 (1995).

(Continued)

*Primary Examiner* — Cephia D Toomer
*Assistant Examiner* — Vishal Vasisth
(74) *Attorney, Agent, or Firm* — Luedeka Neely Group, P.C.

(57) ABSTRACT

There is disclosed herein an additive composition including a compound of formula (III):

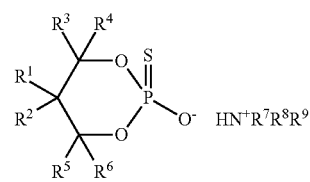

wherein $R^1$, $R^2$, $R^3$, $R^4$, $R^5$, $R^6$, $R^7$, $R^8$, and $R^9$ are independently selected from the group consisting of hydrogen, cyano, and hydrocarbyl groups comprising from about 1 to about 30 carbon atoms.

18 Claims, 1 Drawing Sheet

U.S. PATENT DOCUMENTS

| | | | |
|---|---|---|---|
| 2,224,695 A | 12/1940 | Prutton | |
| 2,284,409 A | 5/1942 | Erath | |
| 2,284,410 A | 5/1942 | Farmer | |
| 2,447,288 A | 8/1948 | Smith et al. | |
| 2,616,905 A | 11/1952 | Asseff et al. | |
| 2,945,749 A | 7/1960 | Andress, Jr. | |
| 3,087,936 A | 4/1963 | Le Suer | |
| 3,172,892 A | 3/1965 | Le Suer et al. | |
| 3,184,411 A | 5/1965 | Lowe | |
| 3,192,162 A | 6/1965 | Bartlett et al. | |
| 3,202,678 A | 8/1965 | Stuart et al. | |
| 3,216,936 A | 11/1965 | Le Suer et al. | |
| 3,219,666 A | 11/1965 | Norman et al. | |
| 3,254,025 A | 5/1966 | Le Suer et al. | |
| 3,272,746 A | 9/1966 | Le Suer et al. | |
| 3,281,428 A | 10/1966 | Le Suer | |
| 3,282,955 A | 11/1966 | Le Suer | |
| 3,338,832 A | 8/1967 | Le Suer | |
| 3,342,735 A | 9/1967 | Reed et al. | |
| 3,344,069 A | 9/1967 | Stuebe | |
| 3,403,102 A | 9/1968 | Le Suer et al. | |
| 3,502,607 A | 3/1970 | Trapasso | |
| 3,511,780 A | 5/1970 | Neblett et al. | |
| 3,513,093 A | 5/1970 | Le Suer | |
| 3,533,945 A | 10/1970 | Vogel | |
| 3,658,836 A | 4/1972 | Vineyard | |
| 3,682,819 A | 8/1972 | Morris et al. | |
| 3,703,536 A | 11/1972 | Piasek et al. | |
| 3,718,663 A | 2/1973 | Piasek et al. | |
| 3,846,317 A | 11/1974 | Lintzenich | |
| 3,984,448 A | 10/1976 | Lippsmeier | |
| 4,234,435 A | 11/1980 | Meinhardt et al. | |
| 4,348,291 A | 9/1982 | Shim | |
| 4,370,247 A | 1/1983 | Ostyn | |
| 4,431,552 A | 2/1984 | Salentine | |
| 4,455,243 A | 6/1984 | Liston | |
| 4,544,492 A | 10/1985 | Zinke et al. | |
| 4,615,826 A | 10/1986 | Erdman | |
| 4,648,980 A | 3/1987 | Erdman | |
| 4,652,387 A | 3/1987 | Andress, Jr. et al. | |
| 4,755,311 A | 7/1988 | Burjes et al. | |
| 4,857,214 A | 8/1989 | Papay et al. | |
| 4,900,460 A | 2/1990 | Cardis | |
| 4,943,672 A | 7/1990 | Hamner et al. | |
| 4,997,968 A | 3/1991 | Burjes et al. | |
| 5,198,133 A | 3/1993 | Papay | |
| 5,240,622 A | 8/1993 | Nesvadba | |
| 5,354,484 A | 10/1994 | Schwind et al. | |
| 5,358,650 A | 10/1994 | Srinivasan et al. | |
| 5,569,644 A | 10/1996 | Geibach et al. | |
| 5,571,445 A | 11/1996 | Srinivasan et al. | |
| 5,698,498 A | 12/1997 | Luciani et al. | |
| 5,767,044 A | 6/1998 | Bigelow et al. | |
| 5,882,505 A | 3/1999 | Wittenbrink et al. | |
| 5,968,880 A | 10/1999 | Mathur et al. | |
| 6,013,171 A | 1/2000 | Cook et al. | |
| 6,080,301 A | 6/2000 | Berlowitz et al. | |
| 6,096,691 A | 8/2000 | Conary et al. | |
| 6,096,940 A | 8/2000 | Wittenbrink et al. | |
| 6,103,099 A | 8/2000 | Wittenbrink et al. | |
| 6,165,949 A | 12/2000 | Berlowitz et al. | |
| 6,180,575 B1 | 1/2001 | Nipe | |
| 6,451,745 B1 | 9/2002 | Ward | |
| 6,528,458 B1 | 3/2003 | Tagliamonte et al. | |
| 6,562,765 B1 | 5/2003 | Boffa | |
| 6,844,300 B2 | 1/2005 | Milner et al. | |
| 6,890,890 B2 | 5/2005 | Gahagan | |
| 6,962,895 B2 | 11/2005 | Scharf et al. | |
| 2002/0010102 A1 | 1/2002 | Kosima et al. | |
| 2003/0096713 A1 | 5/2003 | Schnur et al. | |
| 2003/0166474 A1 | 9/2003 | Winemiller et al. | |
| 2004/0192564 A1 | 9/2004 | Balasubramaniam et al. | |
| 2004/0259743 A1* | 12/2004 | Butke | 508/273 |
| 2005/0059562 A1 | 3/2005 | Garmier | |
| 2005/0059563 A1 | 3/2005 | Sullivan et al. | |
| 2005/0143266 A1 | 6/2005 | Yagishita | |
| 2005/0202979 A1 | 9/2005 | Henly | |
| 2007/0105728 A1 | 5/2007 | Phillips et al. | |

FOREIGN PATENT DOCUMENTS

| | | |
|---|---|---|
| EP | 0 578 435 A1 | 1/1994 |
| EP | 1057883 | 12/2000 |
| EP | 1195426 | 4/2002 |
| EP | 1785476 | 5/2007 |
| GB | 1 268 562 A | 3/1972 |
| GB | 1268561 | 3/1972 |
| GB | 1293245 | 10/1972 |
| GB | 1329978 | 9/1973 |
| WO | WO 87/07638 | 12/1987 |
| WO | 2005/028599 | 3/2005 |

OTHER PUBLICATIONS

Oswald, Alexis A., "Synthesis of Cyclic Phosphorous Acid Esters by Transesteficiation," Can. J. Chem., 37:1498-1504 (1959).

Zwierzak, A., "Cyclic Organophosphorous Compounds. I. Synthesis and Infrared Spectral Studies of Cyclic Hydrogen Phosphites and Thiophosphites," Can. J. Chem., 45(21):2501-12 (1967).

Kumaraswamy, Sudha et al., "Synthesis of New α-Halogeno- and Vinylphosphonates Derived from 5,5-Dimethyl-1,3,2-dioxaphosphinan-2-one,"Synthesis, 2:207-12 (1997).

Edmundson, R. S., "Cyclic Organophosphorus Compounds—III Some Sterically Hindered Pyrophosphates," Tetrahedron, 21:2379-87 (1965).

Patani, George A. et al., Bioisosterism: A Rational Approach in Drug Design, Chem. Rev., 1996, 96, 3147-76, Department of Pharmaceutical Chemistry, College of Pharmacy, Rutgers. The State University of New Jersey, Piscataway, New Jersey 08855-0789.

Kudelska, Wieslawa, Syntheis of glycosyl cyanides by the reaction of 1-S-phosphorothioates of carbohydrates with trimethylsilyl cyanide, Aeitschrift fuer Naturforschung, B: Chemical Sciences (1998), 53 (11), 1277-1280, CAS:130:110480.

Lopusinksi, Andrzej, et al., Reaction of dialkoxythiophosphoranesulfenyl chlorides with dialkyl trimethylsilyl phosphites. New stereoselective route to the unsymmetrical tetraalkyl dithiopyrophosphates. Preparation of diastereoisomeric 2-(trimethylsiloxy)-4 methyl-1, 3, 2 dioxaphosphorinanes, Phosphorus and Sulfur and the Related Elements, 1987, CAS:107:77911.

Zinke, Horst, et al., Lubricating Compositions, Eur. Pat. Appl., 29 pp. 1985, CAS:102:98177.

Via, Francis A., Photopolymerizable composition stabilized with ammonium salts of phosphorus acid and process, 1978, U.S., 9 pp. CODEN: USXXAM, CAS:89:25295.

Milolajczyk, M. et al., Organophosphorus compounds. CLXX. Stereochemistry of organophosphorus cyclic compounds. I. Stereospecific synthesis of cis- and trans-2hydroxy-2-thio and (seleno)-4-methyl-1,3,2-dioxaphosphorinanes, 1973, CAS: 78:58286.

XP-002417703—Beilstein Registry No. 1908909; Jun. 29, 1989.

XP-002427219—Beilstein Registry No. 1859471; Jun. 29, 1989.

Database Beilstein, Beilstein Institute for Organic Chemistry, Frankfurt-Main, DE; XP002427219; Database accession No. 1859471.

M. Mikolajczyk, J. Luczak; "Stereochemistry of Organophosphorus Cyclic Compounds" Tetrahedron, vol. 28, 1972, pp. 5411-5422, XP002417564.

W. Kudelska, M. Michalska: "O,O-Dialkylphosphoro-thioic and -dithioic Acids as Functionalising Reagents of Monosaccharides", Carbohydrate Research, vol. 83, 1980, pp. 43-49, XP002417563.

M. Michalska, J. Michalski, I. Orlich; Glycosylation of Organic Thio- and Selenoacids of Phosphorus: Tetrahedron, vol. 34, 1972, pp. 617-622, XP002424356.

Database Beilstein, Beilstein Institute for Organic Chemistry, Frankfurt-Main, DE; Jun. 29 1989, XP002417703.

D.A. Predvotilev, G.A. Savin, E.E. Nifant'ev: Journal of General Chemistry of the USSR, vol. 62, No. 11, 1992, pp. 2018-2025, XP000383103.

M. Mikolajczyk, P. Kietbasinski, A. Suit: Tetrahedron, vol. 42, No. 16, 1986, pp. 4591-4601, XP002417562.

Olesiak et al, 2002, Synlett, No. 6, p. 967-971.

CA Reg No. 462104-21-8, entered into the STN database on Oct. 17, 2002.

* cited by examiner

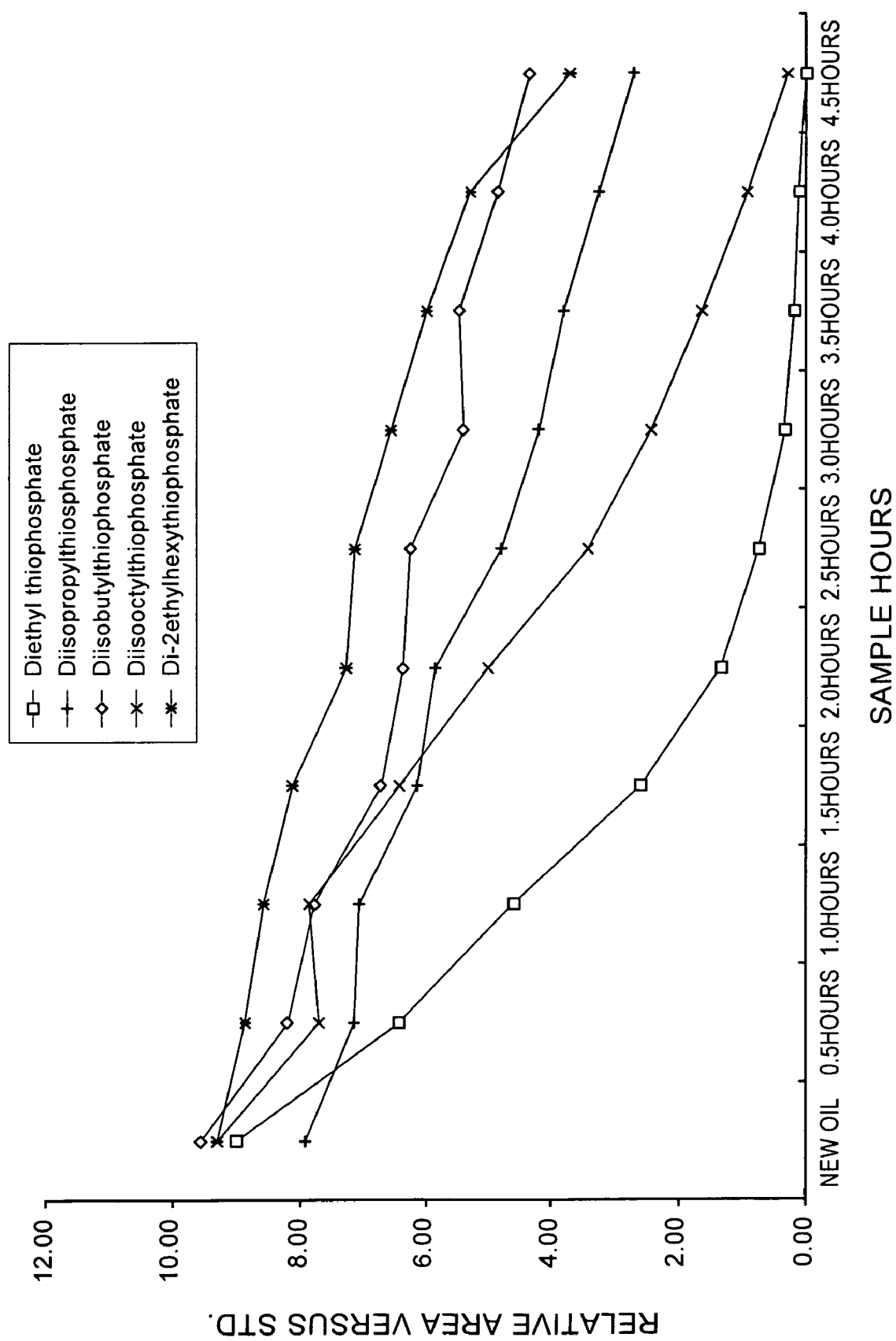

COMPOSITION COMPRISING A SULFUR-CONTAINING, PHOSPHORUS-CONTAINING COMPOUND, AND/OR ITS SALT, AND USES THEREOF

RELATED APPLICATIONS

This application claims the benefit of priority of U.S. provisional application Ser. No. 60/734,757, filed on Nov. 9, 2005.

FIELD OF THE DISCLOSURE

The present disclosure relates to a composition comprising a sulfur-containing, phosphorus-containing compound and/or its salt, and methods of use thereof.

BACKGROUND OF THE DISCLOSURE

The use of phosphorous-containing compounds for use in lubricant compositions is known. In particular, the phosphorous-containing compounds generally comprise linear alkyl chains. However, the problem with these compounds is that they are known to be thermally unstable at elevated temperatures in a fully formulated gear lubricant. A thermally unstable compound is more likely to prematurely decompose in the lubricant composition and would no longer provide a property, such as antiwear, to the lubricant composition.

Lubricant compositions, such as gear oils, typically are subjected to elevated temperatures and therefore it would be beneficial to provide a thermally stable compound that would not prematurely decompose at higher temperatures. A thermally stable compound would therefore remain in the lubricant composition for an extended period of time and provide the property, e.g., antiwear, to the composition over the extended period of time. What is needed is a compound that has the proper thermal stability to sustain its antiwear property.

SUMMARY OF THE DISCLOSURE

In accordance with the disclosure, there is disclosed an additive composition comprising a compound of formula (III):

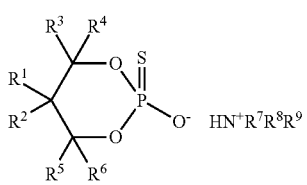

III wherein $R^1$, $R^2$, $R^3$, $R^4$, $R^5$, $R^6$, $R^7$, $R^8$, and $R^9$ are independently selected from the group consisting of hydrogen, cyano, and hydrocarbyl groups comprising from about 1 to about 30 carbon atoms.

There is also disclosed a lubricant composition comprising: a base oil; and at least one of a compound of formulae (II), (III), (V), and (VI):

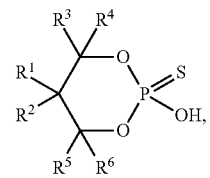

II

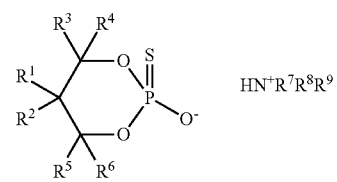

III

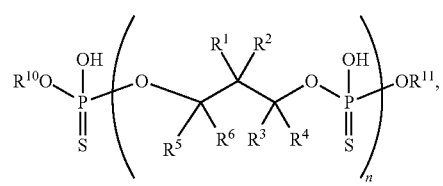

V

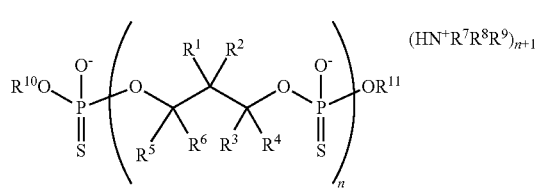

VI wherein n is an integer from 1 to 5; and wherein $R^1$, $R^2$, $R^3$, $R^4$, $R^5$, $R^6$, $R^7$, $R^8$, $R^9$, $R^{10}$, and $R^{11}$ are independently selected from the group consisting of hydrogen, cyano, and hydrocarbyl groups comprising from about 1 to about 30 carbon atoms.

In an aspect, there is disclosed a method of manufacturing a lubricant composition comprising blending a base oil and an additive composition comprising a compound of formula (III):

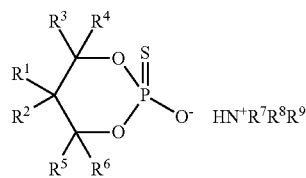

III wherein $R^1$, $R^2$, $R^3$, $R^4$, $R^5$, $R^6$, $R^7$, $R^8$, and $R^9$ are independently selected from the group consisting of hydrogen, cyano, and hydrocarbyl groups comprising from about 1 to about 30 carbon atoms.

In another aspect, there is disclosed an additive composition comprising a reaction product of a nitrogen-containing compound, a neopentyl glycol phosphite, and a sulfur-containing compound.

In a further aspect, there is disclosed a lubricant composition comprising a base oil and a reaction product of a nitrogen-containing compound, a neopentyl glycol phosphite, and a sulfur-containing compound.

In another aspect, there is disclosed a sulfur-containing, neopentyl glycol phosphite having improved antiwear as compared to a non-sulfur-containing, neopentyl glycol phosphite.

In another aspect, there is disclosed a salt of a sulfur-containing, neopentyl glycol phosphite having improved antiwear as compared to a non-sulfur-containing, neopentyl glycol phosphite.

In another aspect, there is disclosed a salt sulfur-containing, neopentyl glycol phosphite having improved antiwear as compared to a sulfur-containing, neopentyl glycol phosphite.

Additional objects and advantages of the disclosure will be set forth in part in the description which follows, and/or can be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

BRIEF DESCRIPTION OF THE DRAWINGS

FIG. 1 is a graph illustrating the thermal stability of various phosphorus-containing species.

DESCRIPTION OF THE EMBODIMENTS

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical);

(2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy);

(3) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, for example no more than one, non-hydrocarbon substituent will be present for every ten carbon atoms in the hydrocarbyl group; typically, there will be no non-hydrocarbon substituents in the hydrocarbyl group.

As used herein, the term "percent by weight", unless expressly stated otherwise, means the percentage the recited component represents to the weight of the entire composition.

The compositions disclosed herein can provide at least one property chosen from improved antiwear protection and improved thermal stability. The composition can be a lubricant composition for use in gears, such as light duty axles and a stationary gear box. It is believed that the disclosed composition can provide at least one of the above-described properties when the axles are subjected to low and/or high temperatures and/or variable load conditions. In an aspect, the disclosed composition can be applied to an axle that has not been broken-in for some time period or distance prior to towing. In an aspect, the light duty axle can be a hypoid gear axle. In another aspect, the disclosed composition can be applied to light duty cars, trucks and sport utility vehicles with or without limited slip mechanisms in the differential experience to improve gear wear protection. The lubricant composition can be suitably used with any friction material such as paper, steel, or carbon fiber.

The composition disclosed herein can be an additive composition comprising at least one of a compound of formulae (II), (III), (V), and (VI), as shown below. The composition disclosed herein can also be a lubricant composition comprising the disclosed additive composition and a base oil. In an aspect, the composition (additive or lubricant) can comprise a reaction product of a nitrogen-containing compound: a phosphorus-containing compound, such as a neopentyl glycol phosphite; and a sulfur-containing compound.

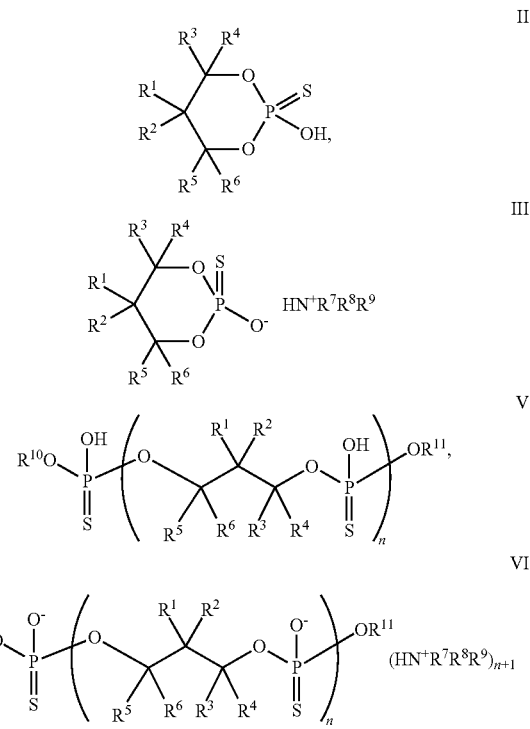

wherein n is an integer from 1 to 5; and
wherein $R^1$, $R^2$, $R^3$, $R^4$, $R^5$, $R^6$, $R^7$, $R^8$, $R^9$, $R^{10}$, and $R^{11}$ are independently selected from the group consisting of hydrogen, cyano, and hydrocarbyl groups comprising from about 1 to about 30 carbon atoms, for example from about 1 to about 20 carbon atoms, and as a further example from about 1 to about 10 carbon atoms.

One of ordinary skill in the art would understand how to make any of the disclosed compounds. For example, a process for making at least one of compounds (III) and (VI) can comprise providing a sulfur-containing compound, a nitrogen-containing compound, and a phosphorus-containing compound. In an aspect, the nitrogen-containing compound is an amide and the process can yield at least one of a compound of formulae (II) and (V), which can be reacted, mixed, and/or combined with an additional nitrogen-containing compound, such as an amine, to yield at least one of a compound of formulae (III) and (VI). In another aspect, the nitrogen-containing compound can be an amine and the reaction, mixture and/or combination can result in complete conversion to a salt, such as the compounds of formulae (III) and (VI).

A phosphorus-containing compound, such as a phosphite or a phosphate can be used in the processes disclosed herein. Methods of making both phosphites and phosphates are known. For example, phosphites can be made by reacting either phosphorous acid or different phosphites with various alcohols. Another synthesis method includes reacting phosphorus trichloride with an excess of alcohol. Moreover, cyclic phosphites can be made by transesterification of phosphites with glycols, which can result in a mixture of monomeric and polymeric products. See Oswald, Alexis A., "Synthesis of Cyclic Phosphorous Acid Esters by Transesterification," *Can. J. Chem.*, 37:1498-1504 (1959); and Said, Musa A., et al., "Reactivity of Cyclic Arsenites and Phosphites: X-ray structures of bis(5,5-dimethyl-1,3,2,-diosarsenan-2-yl)ether and bis (2,4,8,10-tetra-tert-butyl-12H-dibenzo[d,g][1,3,2]dioxarsenocin-6-yl)ether," *J. Chem. Soc.*, 22:2945-51 (1995), the disclosures of which are hereby incorporated by reference. Methods for making cyclic hydrogen thiophosphites are also known, such as by reacting a cyclic chlorophosphite with hydrogen sulfide in the presence of pyridine. See Zwierzak, A., "Cyclic organophosphorus compounds. I. Synthesis and infrared spectral studies of cyclic hydrogen phosphites and thiophosphites, *Can. J. Chem.*, 45:2501-12 (1967), the disclosure of which is hereby incorporated by reference.

In an aspect, the phosphite can be a di- or tri-hydrocarbyl phosphite. Each hydrocarbyl group can have from about 1 to about 24 carbon atoms, or from 1 to about 18 carbon atoms, or from about 2 to about 8 carbon atoms. Each hydrocarbyl group can be independently alkyl, alkenyl, aryl, and mixtures thereof. When the hydrocarbyl group is an aryl group, then it can contain at least about 6 carbon atoms; or from about 6 to about 18 carbon atoms. Non-limiting examples of the alkyl or alkenyl groups include propyl, butyl, hexyl, heptyl, octyl, oleyl, linoleyl, stearyl, etc. Non-limiting examples of aryl groups include phenyl, naphthyl, heptylphenol, etc. In an aspect, each hydrocarbyl group can be independently methyl, propyl, butyl, pentyl, hexyl, heptyl, oleyl or phenyl, for example methyl, butyl, oleyl or phenyl, and as a further example methyl, butyl, oleyl, or phenyl.

Non-limiting examples of useful phosphites include dibutyl hydrogen phosphonate, diisobutyl hydrogen phosphonate, dioleyl hydrogen phosphonate, di($C_{14-18}$) hydrogen phosphonate, triphenyl phosphite, a dihydrocarbyl phosphite such as a compound of formula (I), and a polymeric phosphite, such as a compound of formula (IV), both of which are shown below.

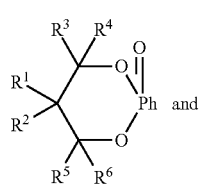

I and

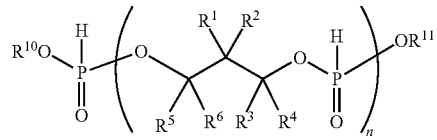

IV wherein n is an integer from about 1 to about 5; and wherein $R^1$, $R^2$, $R^3$, $R^4$, $R^5$, $R^6$, $R^{10}$, and $R^{11}$ are independently selected from the group consisting of hydrogen, cyano, and hydrocarbyl groups comprising from about 1 to about 30 carbon atoms, for example from about 1 to about 20 carbon atoms, and as a further example from about 1 to about 10 carbon atoms. In an aspect, if n is an integer greater than about 5, it is believed, without being limited to any particular theory, that the repeating unit will not completely sulfurize.

In an aspect, in the compound of formula (I), $R^3$, $R^4$, $R^5$, and $R^6$ can be hydrogen; and $R^1$ and $R^2$ can be methyl. This compound is commonly referred to as neopentyl glycol phosphite (NPGP) and is registered with Chemical Abstracts Select under the designation CAS # 4090-60-2 (5,5-dimethyl-1,3,2-dioxaphosphorinan-2-one). In an aspect, in the compound of formula (IV), $R^1$ and $R^2$ can be methyl; $R^3$, $R^4$, $R^5$, and $R^6$ can be hydrogen; and $R^{10}$ and $R^{11}$ can be alkyl groups comprising from about 1 to about 6 carbon atoms. This compound is a polymeric by-product of the manufacturing process of neopentyl glycol phosphite.

The phosphorus-containing compound can also be at least one of a phosphoric acid ester or salt thereof, a reaction product of a phosphorus acid or anhydride and an unsaturated compound, and mixtures of two or more thereof.

A metal dithiophosphate can be prepared by reacting a metal base with at least one thiophosphorus acids, which can be mono- or dithiophosphorus acids.

The phosphorus acid or anhydride can be reacted with an unsaturated compound, including but not limited to, amides, esters, acids, anhydrides, and ethers.

In an aspect, the phosphorus-containing compound, such as a phosphite, can comprise various functional groups that increase the steric hindrance of the compound and therefore increase its resistance to thermal decomposition. In an aspect, the phosphorus-containing compound can be branched at the position beta to the oxygen atom in the hydrocarbyl chain. It is believed that branching at this beta carbon can change, e.g., can improve, the thermal stability of the phosphorus-containing compound in a lubricant composition.

Moreover, the phosphorus-containing compound can be made using components that would increase the resultant compound's steric hindrance. For example, the alcohol used to make, for example, the phosphite can be a beta-branched alcohol. Non-limiting examples of beta-branched alcohols include isobutanol, 2-ethylhexanol, neopentyl glycol, neopentyl alcohol, pristanol, and methyl isobutyl carbinol (MIBC).

The disclosed phosphorus-containing compound can be used as a starting material to yield a sulfur-containing, phosphorus-containing compound. In an aspect, the process for making a sulfur-containing, phosphorus-containing compound can comprise providing a phosphorus-containing compound, such as those described above, a sulfur-containing compound, and a nitrogen-containing compound to yield the sulfur-containing, phosphorus-containing compound. The sulfur-containing, phosphorus-containing compound can provide improved antiwear properties as compared to a non-sulfur-containing, phosphorus-containing compound.

The sulfur-containing compound can be any compound that comprises free and/or active sulfur. Non-limiting examples of sulfur-containing compounds include sulfurized animal or vegetable fats or oils, sulfurized animal or vegetable fatty acid esters, fully or partially esterified esters of trivalent or pentavalent acids of phosphorus, sulfurized olefins, dihydrocarbyl polysulfides, sulfurized Diels-Alder adducts, sulfurized dicyclopentadiene, sulfurized or co-sulfurized mixtures of fatty acid esters and monounsaturated olefin, co-sulfurized blends of fatty acid, fatty acid ester and α-olefin, functionally-substituted dihydrocarbyl polysulfides, thio-aldehydes, thio-ketones and derivatives thereof (e.g., acids, esters, imines, or lactones), epithio compounds, sulfur-containing acetal derivatives, co-sulfurized blends of terpene and acyclic olefins, polysulfide olefin products, and elemental sulfur.

In an aspect, the sulfur-containing compound can be made by reacting an olefin, such as isobutene, with sulfur. The product, e.g., sulfurized isobutylene or sulfurized polyisobutylene, typically has a sulfur content of 10 to 55%, for example 30 to 50% by weight. A wide variety of other olefins or unsaturated hydrocarbons, e.g., isobutene dimer or trimer, can be used to form such sulfur-containing compounds.

In another aspect, polysulfides composed of one or more compounds represented by the formula: $R^{20}$—$S_x$—$R^{21}$ where $R^{20}$ and $R^{21}$ can be hydrocarbyl groups each of which can contain from about 3 to about 18 carbon atoms and x can be in the range of from about 2 to about 8, for example in the range of from about 2 to about 5, and as a further example can be 3. The hydrocarbyl groups can be of widely varying types such as alkyl, cycloalkyl, alkenyl, aryl, or aralkyl. Tertiary alkyl polysulfides such as di-tert-butyl trisulfide, and mixtures comprising di-tert-butyl trisulfide (e.g., a mixture composed principally or entirely of the tri, tetra-, and pentasulfides) can be used. Examples of other useful dihydrocarbyl polysulfides include the diamyl polysulfides, the dinonyl polysulfides, the didodecyl polysulfides, and the dibenzyl polysulfides.

The sulfur-containing compound can be used in at least an equimolar or greater amount per equivalent of phosphorus-containing compound. In an aspect, from about 1 to about 1.5 molar equivalents of the sulfur-containing compound can be used.

The nitrogen-containing compound can be any nitrogen-containing compound, such as an amide of the structure $R^3CONR^4R^5$ wherein $R^3$, $R^4$ and $R^5$ can be each independently hydrogen or a hydrocarbyl group containing from about 1 to about 30 carbon atoms or an ethoxylated amide of the structure

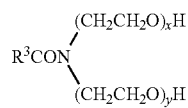

wherein the sum of x and y can be from about 1 to about 50, for example from about 1 to about 20, and as a further example from about 1 to about 10. In an aspect, when $R^3$, $R^4$ and $R^5$ are hydrocarbyl groups, they contain from about 1 to about 18 carbon atoms and for example from about 1 to about 6 carbon atoms.

When $R^3$ is hydrogen and $R^4$ and $R^5$ are hydrocarbyl groups, the nitrogen-containing compound is a dihydrocarbyl formamide. Non-limiting examples of dihydrocarbylformamides having utility herein include: dimethylformamide, diethylformamide, dipropylformamide, methylethylformamide, dibutylformamide, methylbutylformamide, ethylbutylformamide, dioleylformamide, distearylformamide, didecylformamide, ditridecylformamide, decyltridecylformamide, decyloleylformamide, and tridecyloleylformamide, etc.

When $R^3$ is a hydrocarbyl group and $R^4$ and $R^5$ are both hydrogen, the nitrogen-containing compound is a primary hydrocarbyl amide. Non-limiting examples of primary hydrocarbyl amides include acetamide, propionamide, butyramides, valeramide, lauramide, myristamide and palmitamide. Some commercial simple fatty acid amides are available from Armak Company: coco fatty amide, octadecanamide, hydrogenated tallow fatty amide, oleamide, and 13-docosenamide.

When $R^3$ and $R^4$ are both hydrocarbyl groups and $R^5$ is hydrogen, the nitrogen-containing compound is an N-substituted amide. Non-limiting examples of N-substituted amides include N-methylacetamide, N-ethylacetamide, N-methylvaleramide, N-propyllauramide, N-methyloleamide and N-butylstearamide.

When $R^3$, $R^4$ and $R^5$ are all hydrocarbyl groups, the nitrogen-containing compound is an N,N-disubstituted amide. Non-limiting examples of N,N-disubstituted amides include N,N-dimethylacetamide, N-methyl-N-ethylacetamide, N,N-diethylpropionamide, N,N-dibutylvaleramide, N,N-diethylstearamide, and N,N-dimethyloleamide.

Additional non-limiting examples of the nitrogen-containing compound include N,N-bis(2-hydroxyethyl)dodecanamide, N,N-bis(2-hydroxyethyl) coco fatty acid amide, N,N-bis(2-hydroxyethyl)oleamide, N-2-hydroxyethylcocamide, and N-2-hydroxyethylstearamide.

The nitrogen-containing compound can be present in any amount that drives the sulfurization of the phosphorus-containing compound. In an aspect, the nitrogen-containing compound can be present in an amount ranging from about 0.05 to about 2, for example from about 1 to about 1.5 molar equivalents.

In an aspect, the sulfur-containing, phosphorus-containing compound can be at least one of a compound of formulae (II) and (V):

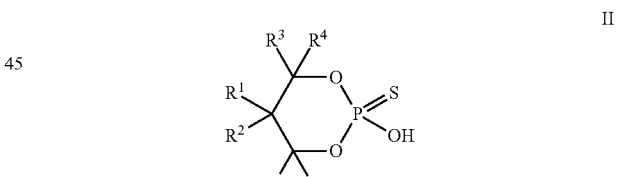

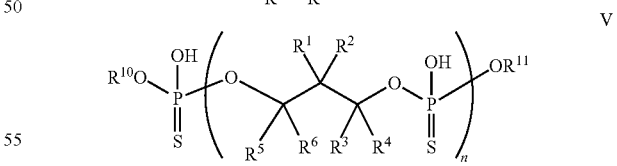

wherein n is an integer from 1 to 5; and
wherein $R^1$, $R^2$, $R^3$, $R^4$, $R^5$, $R^6$, $R^{10}$, and $R^{11}$ are independently selected from the group consisting of hydrogen, cyano, and hydrocarbyl groups comprising from about 1 to about 30 carbon atoms, for example from about 1 to about 20 carbon atoms, and as a further example from about 1 to about 10 carbon atoms.

In an aspect, in formula (II), $R^1$ and $R^2$ can be methyl; and $R^3$, $R^4$, $R^5$, and $R^6$ can be hydrogen. In another aspect, in formula (V), $R^1$ and $R^2$ can be methyl; $R^3$, $R^4$, $R^5$, and $R^6$ can be hydrogen; and $R^{10}$ and $R^{11}$ can be alkyl groups comprising from about 1 to about 6 carbon atoms.

There is also disclosed a process for making a salt. In particular, an additional nitrogen-containing compound can be provided to the sulfur-containing, phosphorus-containing compound to yield a salt. The additional nitrogen-containing compound can be different from the nitrogen-containing compound discussed above in relation to making the sulfur-containing, phosphorus-containing compound. As disclosed above, another process for making a salt of the sulfur-containing, phosphorus-containing compound can comprise providing a nitrogen-containing compound, such as the amines disclosed below, a sulfur-containing compound, and a phosphorus-containing compound, wherein the conversion to the salt is complete. The salt, such as a salt of a sulfurized neopentyl glycol phosphite, can have improved antiwear as compared to a sulfurized neopentyl glycol phosphite and a non-sulfurized neopentyl glycol phosphite.

The disclosed process can include the use of solvents. The solvent can be any inert fluid substance in which at least one of the reactants is soluble or the product is soluble. Non-limiting examples include benzene, toluene, xylene, n-hexane, cyclohexane, naphtha, diethyl ether carbitol, dibutyl ether dioxane, chlorobenzene, nitrobenzene, carbon tetrachloride, chloroform, base oil, such as gas-to-liquid and polyalphaolefin, and process oil.

The additional nitrogen-containing compound can help neutralize any acids. Any nitrogen-containing compound can be used so long as it is soluble in the fully formulated lubricant composition, which can comprise a base oil. Non-limiting examples of the additional nitrogen-containing compound include an amide, an amine, and a heterocyclic compound comprising a basic nitrogen, such as pyridine. In an aspect, the additional nitrogen-containing compound is an amine, which can be primary, secondary, or tertiary.

In an aspect, the hydrocarbyl amines can be primary hydrocarbyl amines comprising from about 4 to about 30 carbon atoms in the hydrocarbyl group, and for example from about 8 to about 20 carbon atoms in the hydrocarbyl group. The hydrocarbyl group can be saturated or unsaturated. Representative examples of primary saturated amines are those known as aliphatic primary fatty amines. Typical fatty amines include alkyl amines such as n-hexylamine, n-octylamine, n-decylamine, n-dodecylamine, n-tetradecylamine, n-pentadecylamine, n-hexadecylamine, n-octadecylamine (stearyl amine), etc. These primary amines are available in both distilled and technical grades. While the distilled grade can provide a purer reaction product, amides and imides can form in reactions with the amines of technical grade. Also suitable are mixed fatty amines.

In an aspect, the amine salts of the disclosed compounds can be those derived from tertiary-aliphatic primary amines having at least about 4 carbon atoms in the alkyl group. For the most part, they can be derived from alkyl amines having a total of less than about 30 carbon atoms in the alkyl group.

Usually the tertiary aliphatic primary amines are monoamines represented by the formula

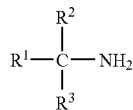

wherein $R^1$, $R^2$, and $R^3$ can be the same or different and can be a hydrocarbyl group containing from about one to about 30 carbon atoms. Such amines are illustrated by tertiary-butyl amine, tertiary-hexyl primary amine, 1-methyl-1-amino-cyclohexane, tertiary-octyl primary amine, tertiary-decyl primary amine, tertiary-dodecyl primary amine, tertiary-tetradecyl primary amine, tertiary-hexadecyl primary amine, tertiary-octadecyl primary amine, tertiary-tetracosanyl primary amine, tertiary-octacosanyl primary amine.

Mixtures of amines are also useful for the purposes of this disclosure. Illustrative of amine mixtures of this type can be a mixture of $C_8$-$C_{16}$ tertiary alkyl primary amines and a similar mixture of $C_{14}$-$C_{24}$ tertiary alkyl primary amines. The tertiary alkyl primary amines and methods for their preparation are well known to those of ordinary skill in the art and, therefore, further discussion is unnecessary. The tertiary alkyl primary amine useful for the purposes of this disclosure and methods for their preparation are described in U.S. Pat. No. 2,945,749, which is hereby incorporated by reference for its teaching in this regard.

Primary amines in which the hydrocarbon chain comprises olefinic unsaturation also can be quite useful. Thus, the R groups can contain at least one olefinic unsaturation depending on the length of the chain, usually no more than one double bond per 10 carbon atoms. Representative amines are dodecenylamine, myristoleylamine, palmitoleylamine, oleylamine and linoleylamine.

Secondary amines include dialkylamines having two of the above alkyl groups including fatty secondary amines, and also mixed dialkylamines where R' can be a fatty amine and R" can be a lower alkyl group (1-9 carbon atoms) such as methyl, ethyl, n-propyl, i-propyl, butyl, etc., or R" can be an alkyl group bearing other non-reactive or polar substituents (CN, alkyl, carbalkoxy, amide, ether, thioether, halo, sulfoxide, sulfone). The fatty polyamine diamines can include mono-or dialkyl, symmetrical or asymmetrical ethylene diamines, propane diamines (1,2, or 1,3), and polyamine analogs of the above. Suitable fatty polyamines include N-coco-1,3-diaminopropane, N-soyaalkyl trimethylenediamine, N-tallow-1,3-diaminopropane, and N-oleyl-1,3-diaminopropane.

The nitrogen-containing compound can be provided in any amount necessary to drive the disclosed process to completion, i.e., if enough nitrogen-containing compound is not present then the phosphorus-containing compound does not completely sulfurize. In an aspect, the nitrogen-containing compound can be provided in an amount ranging from about 0.05 to about 2, and for example, from about 1 to about 1.5 molar equivalent per equivalent of phosphorus-containing compound.

The disclosed process can occur at about room temperature (23° C.) or above, for example at least about 50° C., and as a further example ranging from about 50° C. to about 90° C. Generally, mixing at room temperature for a period ranging from about 1 minute to about 8 hours can be sufficient.

Methods for the preparation of such salts are well known and reported in the literature. See for example, U.S. Pat. Nos. 2,063,629; 2,224,695; 2,447,288; 2,616,905; 3,984,448; 4,431,552; 5,354,484; Pesin et al, Zhurnal Obshchei Khimii, 31(8): 2508-2515 (1961); and PCT International Application Publication No. WO 87/07638, the disclosures of which are hereby incorporated by reference.

The salt of the sulfur-containing compound can be formed separately and then added to a lubricating or functional fluid composition. Alternatively, the salt can be formed when the phosphorus-containing compound, such as the disclosed phosphite, is blended with other components to form the lubricating or functional fluid composition. However, if the salt is formed in situ then it is important to restrict the acids, such as anti-rust components, present in the composition because the acids can react with the nitrogen-containing compound and stop the sulfurization and salt formations.

The salt of a sulfur-containing, phosphorus-containing compound can be oil-soluble, i.e., the hydrocarbyl chains of the salt can be of sufficient length, such as at least six carbon atoms, so that the resultant compound is soluble in a formulated composition. The incorporation of hydrophobic groups can lead to an increase in solubility in a non-polar media. Non-limiting examples of a salt of a sulfur-containing, phosphorus-containing compound include diisobutyl thiophosphoric acid $C_{8-16}$ tertiary alkyl primary amine salt, di-2-ethylhexyl-thiophosphoric acid $C_{8-16}$ tertiary alkyl primary amine salt, and neopentyl glycol thiophosphoric acid $C_{8-16}$ tertiary alkyl primary amine salt. In an aspect, there is contemplated a salt of a dithiophosphoric acid. In another aspect, the salt of the sulfur-containing, phosphorus-containing compound can be at least one of a compound of formulae (III) and (VI) shown below.

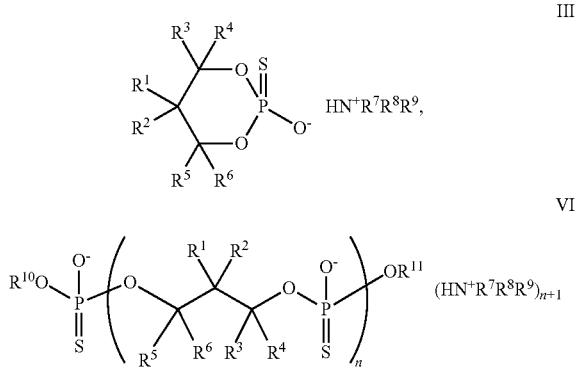

wherein n is an integer from 1 to 5; and wherein $R^1, R^2, R^3, R^4, R^5, R^6, R^7, R^8, R^9, R^{10}$, and $R^{11}$ are independently selected from the group consisting of hydrogen, cyano, and hydrocarbyl groups comprising from about 1 to about 30 carbon atoms, for example from about 1 to about 20 carbon atoms, and as a further example from about 1 to about 10 carbon atoms. In an aspect, in formula (VI), $R^1$ and $R^2$ can be methyl; $R^3, R^4, R^5, R^6, R^7$, and $R^8$ can be hydrogen; $R^9$ can be a tertiary $C_{12-14}$ alkyl group; and $R^{10}$ and $R^{11}$ can be alkyl groups comprising from about 1 to about 6 carbon atoms. In an aspect, in formula (III), $R^3, R^4, R^5, R^6, R^7$, and $R^8$ can be hydrogen; $R^1$ and $R^2$ can be methyl; and $R^9$ can be a tertiary $C_{12-14}$ alkyl group.

Base oils suitable for use in formulating the disclosed compositions can be selected from any of the synthetic or mineral oils or mixtures thereof. Mineral oils include animal oils and vegetable oils (e.g., castor oil, lard oil) as well as other mineral lubricating oils such as liquid petroleum oils and solvent treated or acid-treated mineral lubricating oils of the paraffinic, naphthenic or mixed paraffinic-naphthenic types. Oils derived from coal or shale are also suitable. Further, oils derived from a gas-to-liquid process are also suitable.

The base oil can be present in a major amount, wherein "major amount" is understood to mean greater than or equal to 50%, for example from about 80 to about 98 percent by weight of the lubricant composition.

The base oil typically has a viscosity of, for example, from about 2 to about 15 cSt and, as a further example, from about 2 to about 10 cSt at 100° C. Thus, the base oils can normally have a viscosity in the range of about SAE 50 to about SAE 250, and more usually can range from about SAE 70W to about SAE 140. Suitable automotive oils also include crossgrades such as 75W-140, 80W-90, 85W-140, 85W-90, and the like.

Non-limiting examples of synthetic oils include hydrocarbon oils such as polymerized and interpolymerized olefins (e.g., polybutylenes, polypropylenes, propylene isobutylene copolymers, etc.); polyalphaolefins such as poly(1-hexenes), poly-(1-octenes), poly(1-decenes), etc. and mixtures thereof; alkylbenzenes (e.g., dodecylbenzenes, tetradecylbenzenes, di-nonylbenzenes, di-(2-ethylhexyl)benzenes, etc.); polyphenyls (e.g., biphenyls, terphenyl, alkylated polyphenyls, etc.); alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc., constitute another class of known synthetic oils that can be used. Such oils are exemplified by the oils prepared through polymerization of ethylene oxide or propylene oxide, the alkyl and aryl ethers of these polyoxyalkylene polymers (e.g., methyl-polyisopropylene glycol ether having an average molecular weight of about 1000, diphenyl ether of polyethylene glycol having a molecular weight of about 500-1000, diethyl ether of polypropylene glycol having a molecular weight of about 1000-1500, etc.) or mono- and polycarboxylic esters thereof, for example, the acetic acid esters, mixed $C_{3-8}$ fatty acid esters, or the $C_{13}$ Oxo acid diester of tetraethylene glycol.

Another class of synthetic oils that can be used includes the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.) Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_{5-12}$ monocarboxylic acids and polyols and polyol ethers such as neopentyl glycol, trimethylol propane, pentaerythritol, dipentaerythritol, tripentaerythritol, etc.

Hence, the base oil used which can be used to make the compositions as described herein can be selected from any of the base oils in Groups I-V as specified in the American Petroleum Institute (API) Base Oil Interchangeability Guidelines. Such base oil groups are as follows:

Group I contain less than 90% saturates and/or greater than 0.03% sulfur and have a viscosity index greater than or equal to 80 and less than 120; Group II contain greater than or equal to 90% saturates and less than or equal to 0.03% sulfur and have a viscosity index greater than or equal to 80 and less than 120; Group III contain greater than or equal to 90% saturates and less than or equal to 0.03% sulfur and have a viscosity index greater than or equal to 120; Group IV are polyalphaolefins (PAO); and Group V include all other basestocks not included in Group I, II, III or IV.

The test methods used in defining the above groups are ASTM D2007 for saturates; ASTM D2270 for viscosity index; and one of ASTM D2622, 4294, 4927 and 3120 for sulfur.

Group IV basestocks, i.e. polyalphaolefins (PAO) include hydrogenated oligomers of an alpha-olefin, the most important methods of oligomerisation being free radical processes, Ziegler catalysis, and cationic, Friedel-Crafts catalysis.

The polyalphaolefins typically have viscosities in the range of 2 to 100 cSt at 100° C., for example 4 to 8 cSt at 100° C. They can, for example, be oligomers of branched or straight chain alpha-olefins having from about 2 to about 30 carbon atoms, non-limiting examples include polypropenes, polyisobutenes, poly-1-butenes, poly-1-hexenes, poly-1-octenes and poly-1-decene. Included are homopolymers, interpolymers and mixtures.

Regarding the balance of the basestock referred to above, a "Group I basestock" also includes a Group I basestock with which basestock(s) from one or more other groups can be admixed, provided that the resulting admixture has characteristics falling within those specified above for Group I basestocks.

Exemplary basestocks include Group I basestocks and mixtures of Group II basestocks with Group I bright stock.

Basestocks suitable for use herein can be made using a variety of different processes including but not limited to distillation, solvent refining, hydrogen processing, oligomerisation, esterification, and re-refining.

The base oil can be an oil derived from Fischer-Tropsch synthesized hydrocarbons. Fischer-Tropsch synthesized hydrocarbons can be made from synthesis gas containing $H_2$ and CO using a Fischer-Tropsch catalyst. Such hydrocarbons typically require further processing in order to be useful as the base oil. For example, the hydrocarbons can be hydroisomerized using processes disclosed in U.S. Pat. Nos. 6,103,099 or 6,180,575; hydrocracked and hydroisomerized using processes disclosed in U.S. Pat. Nos. 4,943,672 or 6,096,940; dewaxed using processes disclosed in U.S. Pat. No. 5,882,505; or hydroisomerized and dewaxed using processes disclosed in U.S. Pat. Nos. 6,013,171; 6,080,301; or 6,165,949.

Unrefined, refined and rerefined oils, either mineral or synthetic (as well as mixtures of two or more of any of these) of the type disclosed hereinabove can be used in the base oils. Unrefined oils are those obtained directly from a mineral or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those skilled in the art such as solvent extraction, secondary distillation, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives, contaminants, and oil breakdown products.

Optionally, other components can be present in the lubricant composition or additive composition. Non-limiting examples of other components include other antiwear agents, dispersants, diluents, defoamers, demulsifiers, anti-foam agents, corrosion inhibitors, extreme pressure agents, antioxidants, pour point depressants, seal swell agents, rust inhibitors, and friction modifiers.

Also disclosed herein is a method of lubricating a machine, such as an automotive gear, a stationary gearbox (including an industrial gear), and/or an axle with the disclosed lubricating composition. In an aspect, there is disclosed a method of improving at least one of antiwear protection and thermal stability in a machine, such as an automotive gear, a stationary gearbox (including an industrial gear), and/or an axle comprising placing the disclosed lubricating composition in the machine, such as an automotive gear, a stationary gearbox (including an industrial gear), and/or an axle. There is also disclosed a method of passing ASTM D6121 with lubrited and nonlubrited gear sets, for example at least about 325° F. for at least about 16 hours, and/or a method of maintaining GL-5 and/or SAE J2360 performance comprising lubricating a gear and/or axle with the disclosed lubricating composition.

EXAMPLES

Example 1

Sulfurization of Neopentyl Glycol Phosphite (NPGP) with a Branched Nitrogen-Containing Compound A 1 L reactor equipped with a pressure equalizing addition funnel was charged with sulfur (53.3 g, 1.7 mol), a branched nitrogen-containing compound (PRIMENE® 81R) (320.7 g, 1.7 mol) and 4 cSt polyalphaolefin (375.6 g). An addition funnel was then charged with liquid NPGP (250.04 g, 1.7 mol). The NPGP is a solid at standard conditions and has a melting point ranging from about 60° C. to about 65° C. The additional funnel was heated to avoid solidification.

With stirring and under a blanket of nitrogen, the NPGP was added to the reactor while keeping the mass temperature from about 60 to about 90° C. The rate of the addition was governed by the ability of the reaction system to control the exotherm. The process is exothermic; therefore, cooling of the reaction mass during the addition was required. After the addition was completed, the reaction mixture was stirred at from about 70 to about 90° C. for about 2 to about 6 hours until all of the sulfur was consumed.

The observed P-31 NMR chemical shift (ppm) of the sulfurized NPGP salt was 52.96.

As discussed above, any sulfur-containing compound can be used as the sulfur source so long as there is free and active sulfur. For example, it is envisaged that the following process would also make the disclosed compounds.

A 2 L reactor equipped with a pressure equalizing addition funnel can be charged with 2,5-bis-(t-nonyidithio)-1,3,4-thiadiazole (396.8 g, 0.85 mol), PRIMENE® 81R (320.7 g, 1.7 mol) and 4Cst PAO (375.6 g). The addition funnel could then be charged with liquid NPGP (250.04 g, 1.7 mol). The NPGP is a solid at standard conditions and has a melting point ranging from about 60° C. to about 65° C. The additional funnel can be heated to avoid solidification.

With stirring and under a blanket of nitrogen, the NPGP should be added to the reactor while keeping the mass temperature from about 60 to about 90° C. The rate of the addition is governed by the ability of the reaction system to control the exotherm. After the addition is completed, the reaction mixture can be stirred at from about 70 to about 90° C. for about 2 hours.

Example 2

Sulfurizing Neopentyl Glycol Phosphite (NPGP) with an Amide as the Nitrogen-Containing Compound A 1 L reactor equipped with a pressure equalizing addition funnel can be charged with sulfur (26.7, 0.83 mol), an amide (ETHOMID® O/17) (487.5 g, 0.83 mol) and 4 cSt polyalphaolefin(188.56 g). The addition funnel can then be charged with liquid NPGP (125.0 g, 0.83 mol). The NPGP is a solid at standard conditions and has a melting point ranging from about 60° C. to about 65° C. The additional funnel can be heated to avoid solidification.

With stirring and under a blanket of nitrogen, the NPGP can be added to the reactor while keeping the mass temperature from about 60 to about 90° C. The rate of the addition is governed by the ability of the reaction system to control the exotherm. The process is exothermic; therefore, cooling of the reaction mass during the addition may be required. After the addition is completed, the reaction mixture can be stirred at from about 70 to about 90° C. for about 2 to about 6 hours until all of the sulfur is consumed.

Example 3

Adding an Additional Nitrogen-Containing Compound to Form a Salt

An additional nitrogen-containing compound, such as a branched amine (e.g. PRIMENE® 81R) (153.6 g, 0.83 mol) can then be added to the sulfur-containing compound of Example 2. The mixture can be stirred at 60° C. for 30 minutes.

Example 4

Improved Antiwear

The disclosed sulfur-containing, phosphorus-containing compound, and/or its analogous salt can provide improved antiwear protection, such as required in high temperature modification to the ASTM D-6121 (L-37 Gear Test). It is believed, without being limited to any particular theory, that the beta-branching of the hydrocarbyl groups on the sulfur-containing, phosphorus-containing compound and/or its analogous salt can provide improved thermal stability as compared to compounds that do not contain beta-branching and/or sulfur.

FIG. 1 is a graph demonstrating that the disclosed phosphorus-containing compound and/or its analogous salt exhibited improved stability as compared to other compounds that did not contain beta-branching of its hydrocarbyl groups.

The potential of the antiwear effectiveness was measured by the duration of the phosphorous species at an elevated temperature. A fully formulated gear fluid was placed in a heated bath at about 325° F. Aliquots of the fully formulated gear fluid were pulled at timed intervals and the $^{31}$Phosphorus Nuclear Magnetic Resonance (NMR) spectrum was taken. The phosphorus species observed in the $^{31}$Phosphorus NMR spectrum were plotted versus time and thermal decomposition. A profile for the phosphorus antiwear species was created. The rate or amount of decomposition of the phosphorus species was dependant on the chemical structure of the alkyl chain. Examples of the phosphorus antiwear components were the dialkyl-thiophosphoric acid amine salts. The changes to the alkyl branching changed the thermal decomposition rate of the dialkylthiophosphoric acid amine salts in the heat bath at 325° F. The thermal stabilization was most effective when the beta carbon to the phosphorus-oxygen bond was branched with methyl or a high homolog alkyl group. Examples of the increased stability as demonstrated by a shallower slope are shown in FIG. 1.

Example 5

Lubricant Composition

A lubricant composition was prepared using known techniques and processes. The quantities used to prepare this lubricant composition are provided in Table 1.

TABLE 1

| Component | Weight Percent |
|---|---|
| Formula III | 0.20-1 |
| Base Oil | 40-90 |
| Olefin Copolymer VII (s) | 0-20 |
| Seal Swell Agent (s) | 0-10 |
| EP/AW Agent (s) | 4-6 |
| Pour Point Depressant (s) | 2.5-5 |
| Dispersant (s) | 0.5-4 |
| Amine Rust Inhibitor (s) | 1-2 |
| Anti-Foam Agent (s) | 0.1-2 |
| Demulsifier (s) | 0-0.5 |
| Corrosion Inhibitor (s) | 0.1-1 |

Example 6

L-37 Low and High Temperature Test

Three formulations were prepared. One formulation comprised a compound of Formula III. Another formulation did not comprise a compound of Formula III. And the third formulation comprised a thiophosphate containing non-branched alkyl groups. These formulations were subjected to the High Temperature (325° C. for 16 hours) L-37 Low Speed/High Torque Axle Test (ASTM D-6121). Table 2 shows the High Temperature L-37 passing conditions.

TABLE 2

| Observation | Passing Rating (10 Max) |
|---|---|
| Broken Teeth | NO |
| Wear | >5 |
| Rippling | >8 |
| Ridging | >8 |
| Pitting/Spalling | >9.3 |
| Scoring | 10 |

The results of the test are shown in Table 3.

TABLE 3

High Temperature L-37 Results

| Description | HT L-37 Result |
|---|---|
| Gear oil with no Formula III | FAIL |
| Gear oil with Formula III | PASS |
| Gear oil with linear dialkyl thiophosphate | FAIL |

The results indicate that a composition comprising the disclosed salt of a sulfur-containing, phosphorus-containing compound exhibited improved thermal stability as compared to formulations that did not contain the disclosed compound.

One of ordinary skill in the art would understand that the disclosed compounds are more thermally stable and therefore do not decompose at low temperatures, such as in the L-37 low temperature test, and provide antiwear protection at high temperatures, such as in the L-37 high temperature modification test. Because the disclosed compounds have improved thermal stability they are able to provide antiwear properties to the composition for an extended period of time as compared to other compounds.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," include plural referents unless expressly and unequivocally limited to one referent. Thus, for example, reference to "an antioxidant" includes two or more different antioxidants. As used herein, the term "include" and its grammatical variants are intended to be non-limiting, such that recitation of items in a list is not to the exclusion of other like items that can be substituted or added to the listed items.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A lubricant composition comprising:
   a base oil; and
   at least one of a compound of formulae (II), (III), (V), and (VI):

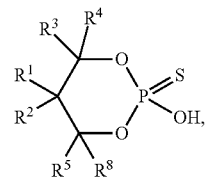

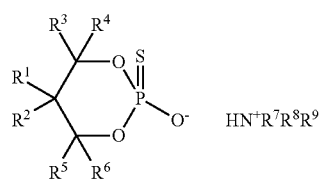

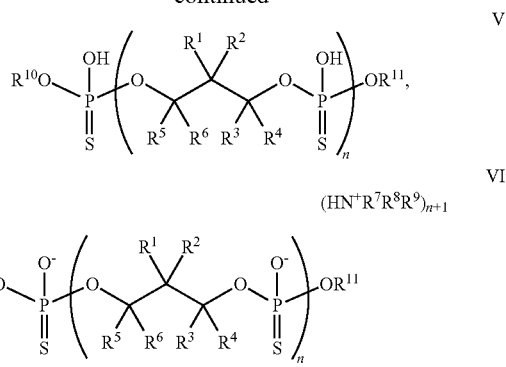

wherein n is an integer from 2 to 5; and
wherein $R^1, R^2, R^3, R^4, R^5, R^6, R^7, R^8, R^9, R^{10}$, and $R^{11}$ are independently selected from the group consisting of hydrogen, cyano, and hydrocarbyl groups comprising from about 1 to about 30 carbon atoms.

2. The composition of claim 1, wherein at least one of a compound of formulae (II), (III), (V), and (VI) is present in the lubricant composition in an amount ranging from about 0.25 wt. % to about 50 wt. % relative to the total weight of the lubricant composition.

3. The composition of claim 1, wherein the base oil is chosen from mineral and synthetic oils.

4. The composition of claim 1, wherein the base oil is a gas-to-liquid base oil.

5. The composition of claim 1, further comprising at least one additive chosen from antiwear agents, dispersants, diluents, defoamers, demulsifiers, anti-foam agents, corrosion inhibitors, extreme pressure agents, antioxidants, pour point depressants, seal swell agents, rust inhibitors, and friction modifiers.

6. A method of manufacturing a lubricant composition comprising blending a base oil and an additive composition comprising a compound of formula (III):

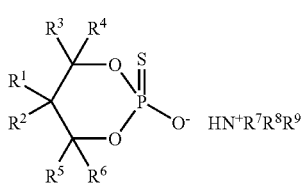

wherein $R^1, R^2, R^3, R^4, R^5, R^6, R^7, R^8$, and $R^9$ are independently selected from the group consisting of hydrogen, cyano, and hydrocarbyl groups comprising from about 1 to about 30 carbon atoms.

7. A method of lubricating an automotive gear comprising using as the lubricant the lubricant composition of claim 1.

8. A method of improving antiwear protection in an automotive gear comprising placing a lubricant composition according to claim 1 in the automotive gear.

9. A method of improving thermal stability in an automotive gear comprising placing a lubricant composition according to claim 1 in the automotive gear.

10. A method of lubricating an axle comprising using as the lubricant the lubricant composition of claim 1.

11. A method of improving antiwear protection in an axle comprising placing a lubricant composition according to claim 1 in the axle.

12. A method of improving thermal stability in an axle comprising placing a lubricant composition according to claim 1 in the axle.

13. A method of lubricating a stationary gearbox comprising using as the lubricant the lubricant composition of claim 1.

14. A method of improving antiwear protection in a stationary gearbox comprising placing a lubricant composition according to claim 1 in the stationary gearbox.

15. A method of improving thermal stability in a stationary gearbox comprising placing a lubricant composition according to claim 1 in the stationary gearbox.

16. A method of passing ASTM D6121 with lubrited and nonlubrited gear sets comprising lubricating a gear with a lubricant composition according to claim 1.

17. A method of passing ASTM D6121 with nonlubrited gear sets at least about 325° F. for at least about 16 hours comprising lubricating a gear with a lubricant composition according to claim 1.

18. A method of maintaining GL-5 and/or SAE J2360 performance comprising lubricating a gear with a lubricant composition according to claim 1.

* * * * *